_US005568251A_

United States Patent [19]

Davies et al.

[11] Patent Number: 5,568,251
[45] Date of Patent: Oct. 22, 1996

[54] AUTHENTICATING SYSTEM

[75] Inventors: Michael Davies; Jerzy A. Dobrowolski, both of Ottawa, Canada

[73] Assignee: National Research Council of Canada, Ottawa, Canada

[21] Appl. No.: 216,451

[22] Filed: Mar. 23, 1994

[51] Int. Cl.$^6$ ........................ G07D 7/00
[52] U.S. Cl. ........................ 356/71
[58] Field of Search ............... 356/71; 359/589

[56] References Cited

U.S. PATENT DOCUMENTS

| | | | |
|---|---|---|---|
| 3,858,977 | 1/1975 | Baird et al. | 356/71 |
| 3,948,345 | 4/1976 | Rosencwaig | 356/432 |
| 4,881,268 | 11/1989 | Uchida et al. | 356/71 |
| 4,908,516 | 3/1990 | West | 356/71 |

OTHER PUBLICATIONS

G. Raybon et al., 1.7Gbit/s Transmission over 217km using a 16×1 photonic integrated circuit transmitter, Electronics Letters vol. 29, No. 14, 1993. pp. 1295–1296.
C. Cremer et al., Grating Spectrograph Integrated with Photodiode Array InGaAsP/InGaAs/InP, 1992 IEEE.
J. B. D. Soole et al., Monolithic InP/InGaAsP/InP Grating Spectrometer for the 1.48–1.56 μm Wavelength Range, Appl. Phys. Lett. vol. 58, No. 18, 6 May 1991 pp. 108–110.
M. Fallahi, et al, Demonstration of Grating Demultiplexer in GaAs/AlGaAs Suitable for Integration, Electronics Letters 19 Nov. 1992, vol. 28, No. 24, p. 2217.
J. A. Dobrowolski et al., Optical Interference Coatings for Inhibiting of Counterfeiting, Optica Acta, 1973, vol. 20, No. 12, pp. 925–937.
A. Moore, New Life for GaAs Emitters, III–Vs Review, Vo. 6. No. 5 pp. 41–44.
J. B. D. Soolé et al, Wavelength–selectable Laser Emission from a Multistripe Array Grating Integrated Cavity Laser, Appl. Phys. Lett. 61 (23) Dec. 1992, pp. 2750–2752.

*Primary Examiner*—Richard A. Rosenberger
*Attorney, Agent, or Firm*—Neil Teitelbaum

[57] ABSTRACT

An authenticating system for verifying articles is provided. The articles to be verified have a thin film multilayer coating applied to them that serves or functions as a type of finger print. In a reflective mode of operation the coating is designed to reflect light radiation of predetermined wavelengths and substantially absorbing or transmitting light radiation of other predetermined wavelengths irradiating a same location on the coating surface; in operation a light source is provided for irradiating light onto said location on the coating surface; and a detector is used to determine the presence and absence within predetermined limits of each of said predetermined wavelengths of light at said location that are substantially reflected by the coating. The system may also be configured in a transmissive mode or an absorptive mode of operation when used with the compatible detection schemes as exemplified herein.

11 Claims, 8 Drawing Sheets

Wavelength

AUTHENTICATING SYSTEM

FIELD OF THE INVENTION

This invention relates generally to a system for determining the authenticity of objects.

BACKGROUND OF THE INVENTION

Systems relating to the authentication of objects such as documents, passports, credit cards and currency often use an anti-counterfeiting means in the form of indicia that are difficult to identify or copy in the hopes of deterring a would-be counterfeiter from making unauthorized copies. For example, decorative or identifiable distinctive marks on currency offer limited protection. However, as more sophisticated anti-counterfeiting means are used, it is usually only a matter of time until even these means are successfully but illegitimately copied.

Currently, optically-variable security devices, such as thin films, holograms, gratings, and micro-prisms, are commonly used to protect valuable documents and credit cards; their optical features can be easily recognized by the public at large. Thin film optically-variable devices are described in a paper entitled Optical Interference Coatings for Inhibiting of Counterfeiting by J. A. Dobrowolski et at. in Optica Acta, 1973, Vol. 20, No. 12, 925–937. Optically-variable thin film security devices exhibiting a color change with a shift in viewing angle have also been disclosed in U.S. Pat. No. 3,858,977 issued in January of 1975 in the names of Baird et al. Such devices are used on large denominations of Canadian bank notes and on drivers' licenses in some jurisdictions, however, the efficacy of these devices is questionable. In an attempt to offer additional security protection U.S. Pat. No. 5,009,486 issued Apr. 23, 1991 in the names of Dobrowolski et al. describes a form depicting, optical interference authenticating device. Dobrowolski et al. teach the introduction of additional patterns in thin film security devices by using masks during their deposition or by laser ablation to remove one or more layers of the thin film system.

Since these and many other security devices depend largely on verification by visual inspection, a person performing the verification must be aware of what features to look for and must possess the visual acuity to perform the task; this is not always the case. As counterfeiters become more successful in their attempts to copy security devices, it is believed that in the future there will be a need for additional security.

OBJECT OF THE INVENTION

In view of the limitations and drawbacks of the aforementioned prior art security devices, it is an object of this invention to provide a security system that will for some time be difficult to counterfeit.

It is another object of the invention to provide a system that includes a detector for detecting the presence or absence at particular wavelengths of absorption, reflection or transmission of light incident upon a protected object, thereby obviating the requirement for visual inspection of the object to ensure its authenticity.

It is another object of the invention to provide a secure key for use by a reader including a detector for detecting the presence or absence at particular wavelengths of absorption, reflection or transmission of light incident onto the key.

SUMMARY OF THE INVENTION

In accordance with the invention, there is provided, a system for authenticating a substrate, operable in one of a first mode, a second mode, and a third mode of operation, the authenticating system in the first mode accepting a reflective substrate, in the second accepting a transmissive substrate and the system in the third mode accepting an absorptive substrate, the authenticating system comprising:

means for irradiating the substrate with light radiation, in the first mode the substrate being coated with a coating capable of reflecting light of predetermined wavelengths and substantially absorbing or transmitting light of other predetermined wavelengths incident upon a same location on the surface of the substrate, in the second mode the substrate being coated with a coating capable of transmitting light of predetermined wavelengths and substantially absorbing or reflecting light of other predetermined wavelengths incident upon a same location on the surface of the substrate, and in the third mode of operation, the substrate being coated with a coating capable of absorbing light of predetermined wavelengths and substantially reflecting or transmitting light of other predetermined wavelengths incident upon a same location on the surface of the substrate; and, detecting means operable in one of the first mode, the second mode and the third mode of operation, in the first mode of operation said means for detecting the presence or absence of each of said predetermined wavelengths of light at the location that in the first mode are substantially reflected off the coating onto said detecting means, in the second mode of operation, said means for detecting the presence or absence of each of said predetermined wavelengths of light at the location that in the second mode are substantially transmitted through the coated substrate onto said detecting means, and in the third mode of operation said means for detecting the presence or absence of each of said predetermined wavelengths of light at the location that in the first mode are substantially absorbed by coating.

In accordance with another aspect of the invention, there is provided, a method for authenticating one of (a) a reflective coated substrate being capable of reflecting light of predetermined wavelengths and substantially absorbing or transmitting light of other predetermined wavelengths incident upon a same location on the coating surface, (b) an absorptive coated substrate being capable of absorbing light of predetermined wavelengths and substantially reflecting or transmitting light of other predetermined wavelengths incident upon a same location on the coating surface, and (c) a transmissive coated substrate being capable of transmitting light radiation of predetermined wavelengths and substantially absorbing or reflecting light radiation of other predetermined wavelengths irradiating a same location on the coating surface, said method comprising the steps of:

irradiating the coating on the substrate with predetermined wavelengths of light radiation; and, performing one of the following steps:

(i) in the case of the reflective coated substrate, detecting the presence or absence of each of said predetermined wavelengths of light incident upon the location, within predetermined limits, that are substantially reflected by the coating; in the case (ii) in the case of the transmissive coated substrate, detecting the presence or absence of each of said predetermined wavelengths of light incident upon the location, within predetermined limits, that are substantially transmitted by the coating; and, (iii) in the case of the absorptive coated substrate detecting the presence or absence of each of said predetermined wavelengths of light incident upon the location, within predetermined limits, that are substantially absorbed by the coating;

In accordance with yet another aspect of the invention, there is provided, an absorption detector comprising, a chamber having a sealable opening for accepting a substrate for contact therewith, said substrate covering and sealing the opening when placed in position for use, thereby forming an airtight acoustic chamber; means for irradiating the substrate in contact with the chamber with a plurality of wavelengths of light; and, an acoustic detector coupled to the chamber for detecting a sound waves characteristic of the absorption of the irradiated light upon a portion of the substrate.

In accordance with yet another aspect of this invention, there is provided, a key comprising a substrate having a thin film multilayer coating thereon, said coating for substantially preventing predetermined wavelengths of light from being transmitted therethrough or reflected therefrom and allowing other predetermined wavelengths of light to be transmitted therethrough or to be reflected therefrom so that they may be detected by a detector.

BRIEF DESCRIPTION OF THE DRAWINGS

Exemplary embodiments of the invention will be described with the aid of drawings, in which.

DETAILED DESCRIPTION

Optical thin films can be used as security devices against counterfeiting in several ways. In this invention it is not the visible colour change with angle of viewing of thin film multilayer coatings that is of particular interest, but the normal or near-normal spectral absorptance, transmittance, and reflectance of the film system itself.

A thin film structure may have as few as one or two layers or may consist of more than 100 layers. Multilayer coatings can be designed that reflect, transmit or absorb incident light of different wavelengths by different, predetermined mounts. It is therefore possible to design system that can be used with different detection schemes.

Characteristics of three typical thin film multilayer coatings suitable for the present application will now be described with reference to Table 1 below:

TABLE 1

| Layer No. | Reflection System d(mm) | Reflection System material | Transmission System d(mm) | Transmission System material | Absorption System d(mm) | Absorption System material |
| --- | --- | --- | --- | --- | --- | --- |
| substrate | | plastic | | plastic | | plastic |
| 1 | 0.0479 | Inconel | 0.0027 | Aluminum | 0.0197 | Inconel |
| 2 | 0.6294 | HfO$_2$ | 2.62755 | SiO$_2$ | 0.5042 | SiO$_2$ |
| 3 | 0.6065 | SiO$_2$ | 1.1776 | HfO$_2$ | 0.7383 | HfO$_2$ |
| 4 | 0.4439 | HfO$_2$ | 0.0003 | Inconel | 106571 | SiO$_2$ |
| 5 | 2.4211 | SiO$_2$ | | | 0.4370 | HfO$_2$ |
| 6 | | | | | 0.4939 | SiO$_2$ |
| medium | | air | | air | | air |
| S(d) | 4.1488 | | 3.8081 | | 3.8502 | |

Referring to Table 1 above, three coatings were designed having the same reflectance, transmittance and absorptance values at the wavelength of 1.30, 1.38, 1.46 and 1.54 mm. These exemplary wavelengths were chosen because they span the spectral region for which laser diodes are readily available. Quite arbitrarily the values at these wavelengths were set to 0.7, 0.3, 0.6 and 0.4, respectively.

For design purposes it was assumed that the coatings would be attached to a plastic or paper substrate, and that the incident medium would be air. Similar solutions can be found for devices such as credit cards, that are embedded in plastic. Two dielectric (SiO$_2$, and HfO$_2$) and two metal (aluminium, Inconel) coating materials were selected. Of course, other materials could be used. However, the chosen materials were selected for the designs because they are commonly used in laboratory settings, are readily available, and are relatively stable. It is possible that better solutions could be found if one were to use more coating materials, but it is unlikely that one would consider this in practice.

Figure 5:
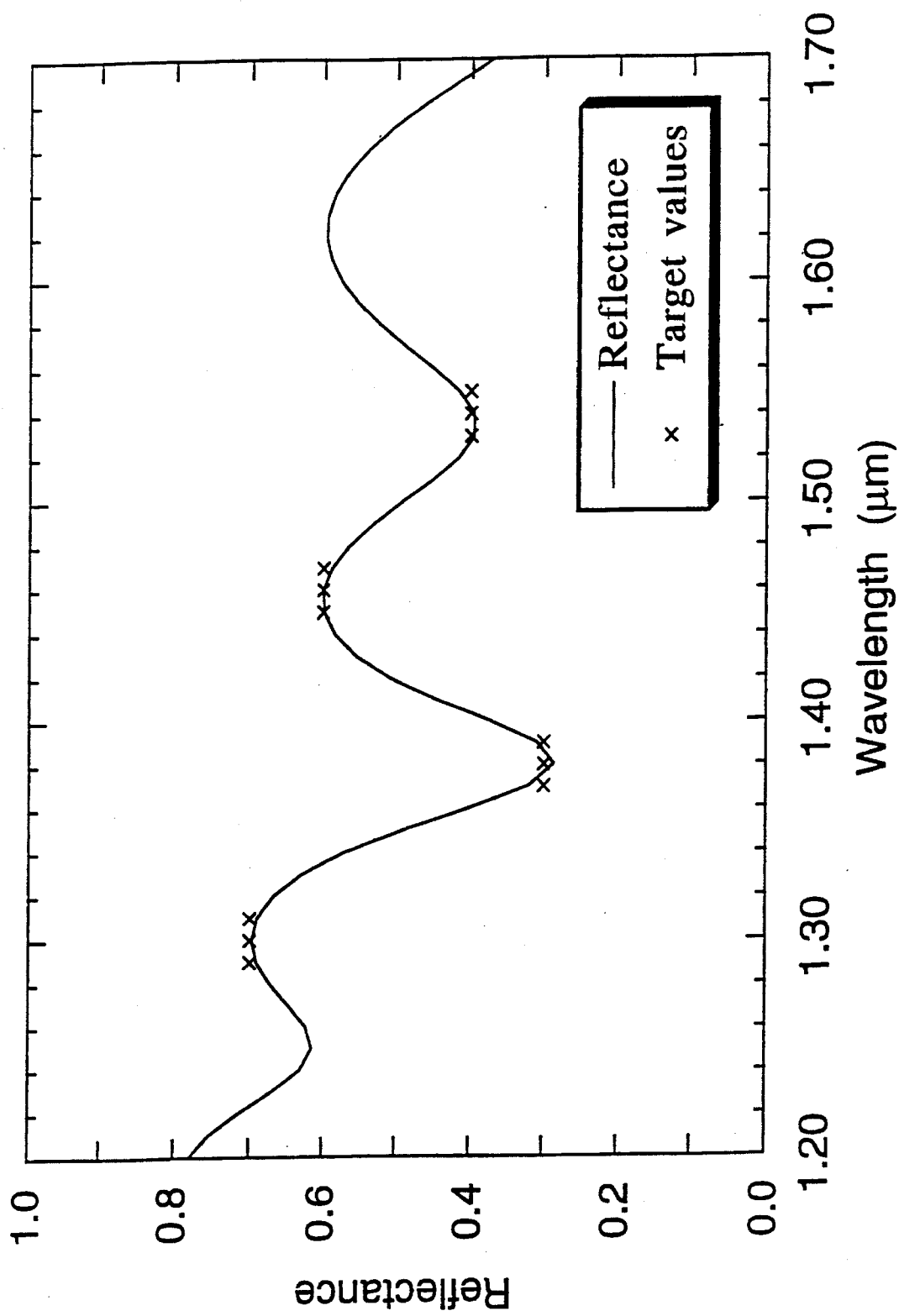
FIG. 5 is a graph representing the reflectance in the 1.2 to 1.7 mm spectral region of a multilayer system designed for use in reflected light and having particular reflectance values at four specific wavelengths.

The first coating, designed for use in reflected light, was directed to one of the preferred embodiments of this invention. The thicknesses of a 5 layer system whose spectral reflectance agreed well with the required target values (represented in the diagrams by crosses) are given in columns 2 and 3 of the table. The spectral performance of the system in the 1.2 to 1.7 mm spectral region is shown in FIG. 5. Solutions were sought in which the reflectance would be either a maximum or a minimum at each of the specified wavelengths, resulting in a more stable and somewhat more forgiving system with respect to errors in thicknesses and optical constants.

The overall metric thickness Â(d) of the multilayer depends on the mean wavelength of the detectors, on the distance between adjacent wavelengths, and on the refractive indices of the dielectric coating materials used. Although the overall thickness of the above filter (4.15 mm)is high, a significant reduction in the metric thickness (by perhaps a factor of 2) is expected should Si be used as the high index coating material. If the detection were carried out in the ultraviolet region at about 0.3 mm, the overall thickness of the system could be reduced by a factor of about 4.

Because of its rather high overall thickness, the coating may be too expensive for the protection of low cost documents, such as bank notes, if present-day deposition technologies are used. However, in the future one can expect further improvements and cost reductions in this area.

Figure 6:
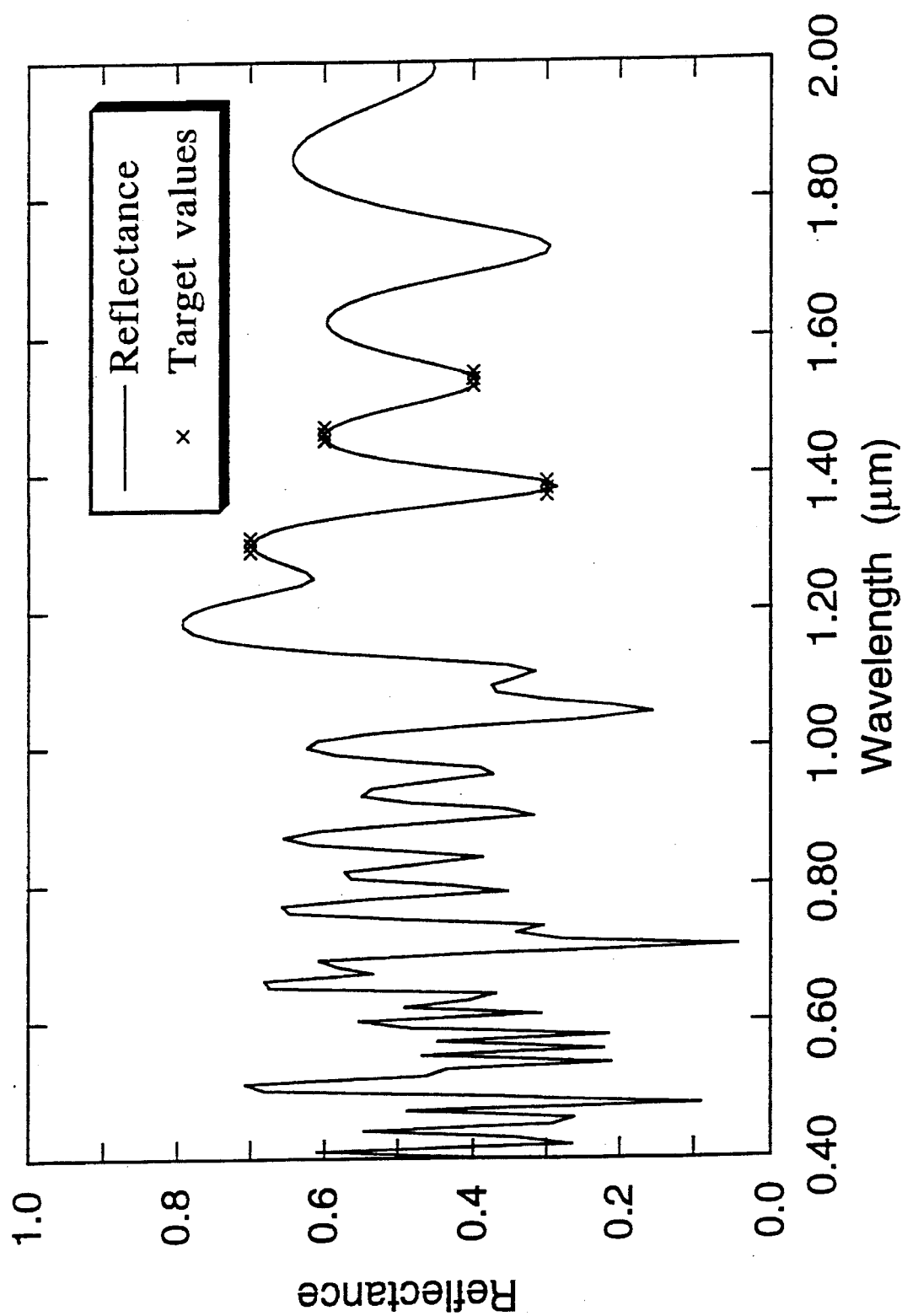
FIG. 6 is a graph representin the spectral reflectance of the multilayer corresponding to FIG. 5, but plotted over the extended wavelength range of 0.4 to 2.00 mm.

FIG. 6 shows the calculated reflectance of the above multilayer over a more extended spectral region. Because of the large overall thickness, there are very many maxima and minima in the visible spectral region (0.38–0.78 mm). As a result, the color of the coating will be rather desaturated and it is believed that the changes in color observed on tilting the coating will not be very pronounced. As stated before, in this the coatings for the present invention differ essentially from those described in U.S. Pat. No. 3,858,977 issued in January of 1975 in the names of Baird et at.

Figure 7:
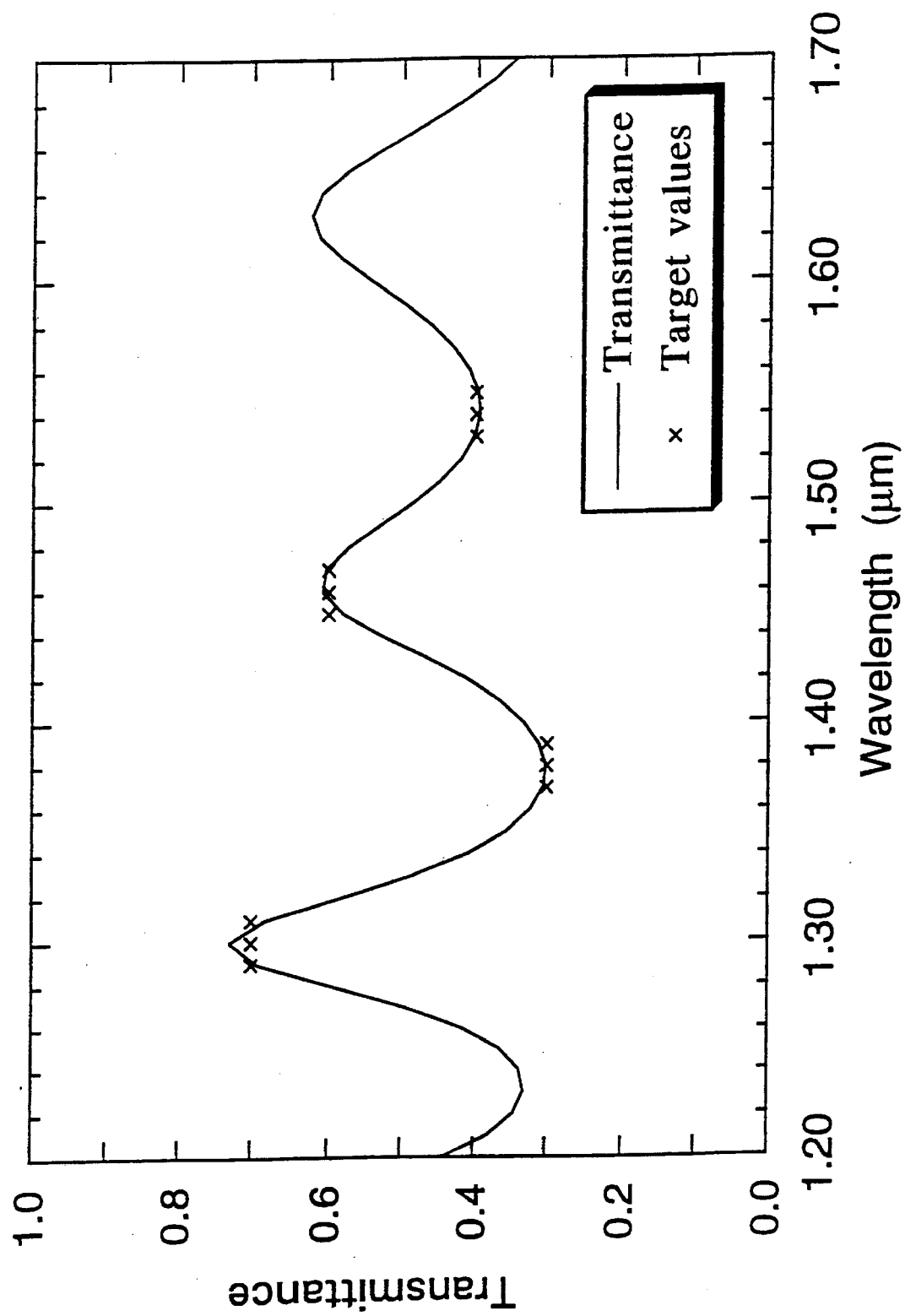
FIG. 7 is a graph representing the transmittance in the 1.2 to 1.7 mm spectral region of a multilayer system designed for use in transmitted light and having particular transmittance values at four specific wavelengths; and, FIG. 8 is a graph representing the absorptance in the 1.2 to 1.7 mm spectral region of a multilayer system designed for use in absorbed light and having particular absorptance values at four specific wavelengths.

FIG. 7 shows the transmittance of a 4 layer system designed to be mounted on a transparent substrate. The construction parameters of the system are given in columns 4 and 5 of table 1. Because the system is viewed in transmission, the thicknesses of the aluminum and Inconel films are much thinner. The deposition of a 3 Ångstrom thick Inconel layer and of the very thin aluminium layer may be difficult to control. Even a slight oxidation of this layer with time would produce a significant change in the spectral transmittance. The overall thickness of this multilayer is not too different from that of the reflection system.

Figure 8:
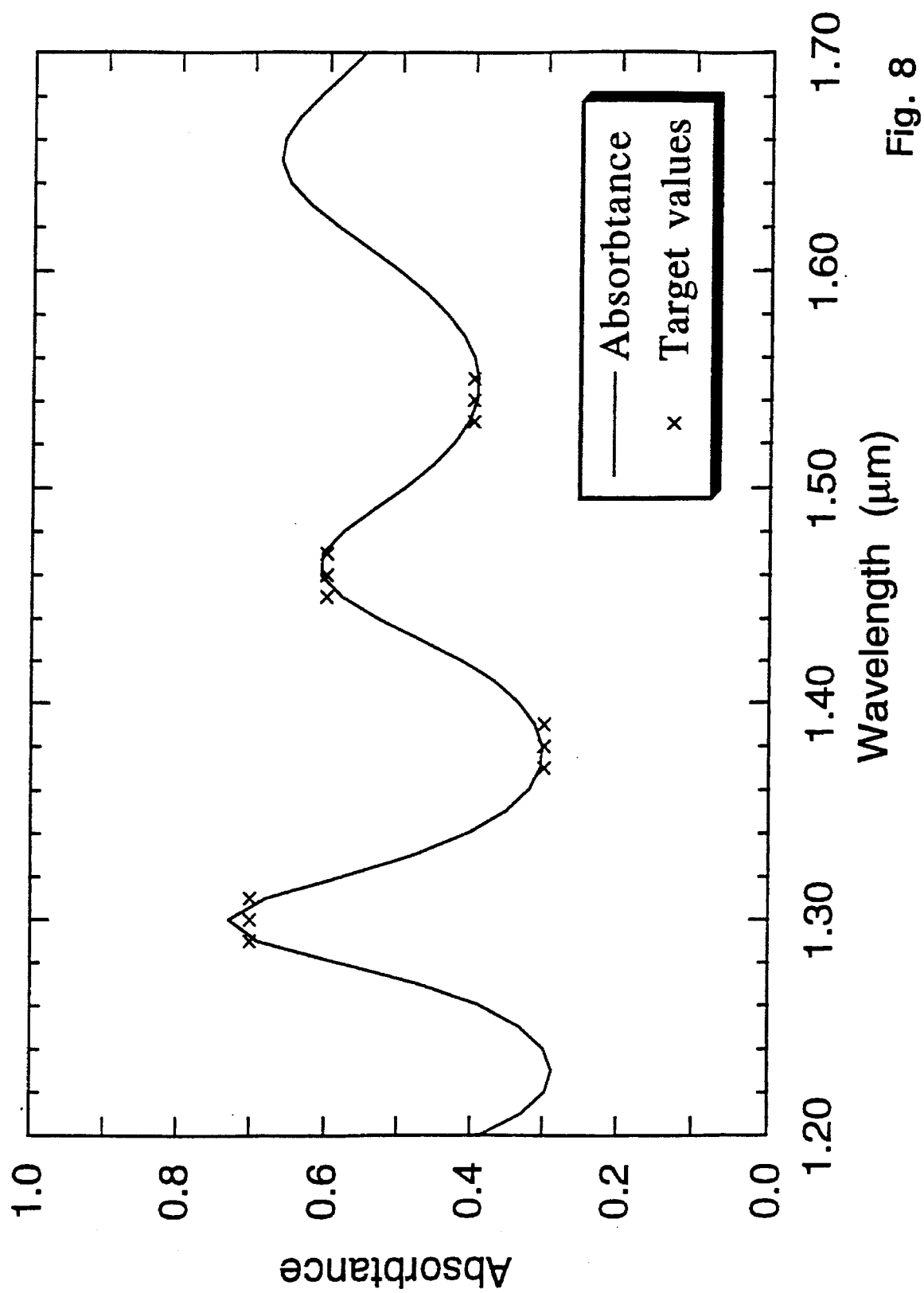

FIG. 8 shows the spectral absorptance of the six layer system whose parameters are given in column 6 and 7 of the table. This layer system would have to be used with a detector such as the one shown in FIG. 4. The correspondence between the target and the calculated performance is more than satisfactory.

The target values chosen assumed that the detecting system can measure the relative intensities of the transmitted, reflected or absorbed radiation at the four wavelengths. It should also be possible to design purely binary-type coatings in which the signal is essentially suppressed at some of the wavelengths. However, a system based on the absolute presence or absence of radiation of particular wavelengths will have, as previously mentioned, a much smaller number of possible "signatures".

In the first design attempt uniformly good results have been obtained for all three coatings. The solutions based on reflected and absorbed radiation use only one somewhat thicker Inconel layer. This alloy is much more stable than aluminium, as are the two oxides. It is believed that these two systems are more practical than the coating designed for use in transmission.

Those skilled in the art will appreciate that the above coatings are only a few examples of the very many different embodiments that fall within the scope of this invention. It is clearly possible to design coatings with performances that are specified at fewer or at more wavelengths and having different target values. In particular, it is possible to design coatings in which the wavelengths are specified at much closer intervals, even to a few nanometers. However, this will require higher overall thicknesses which will be reflected in the cost of the device.

Figure 1:
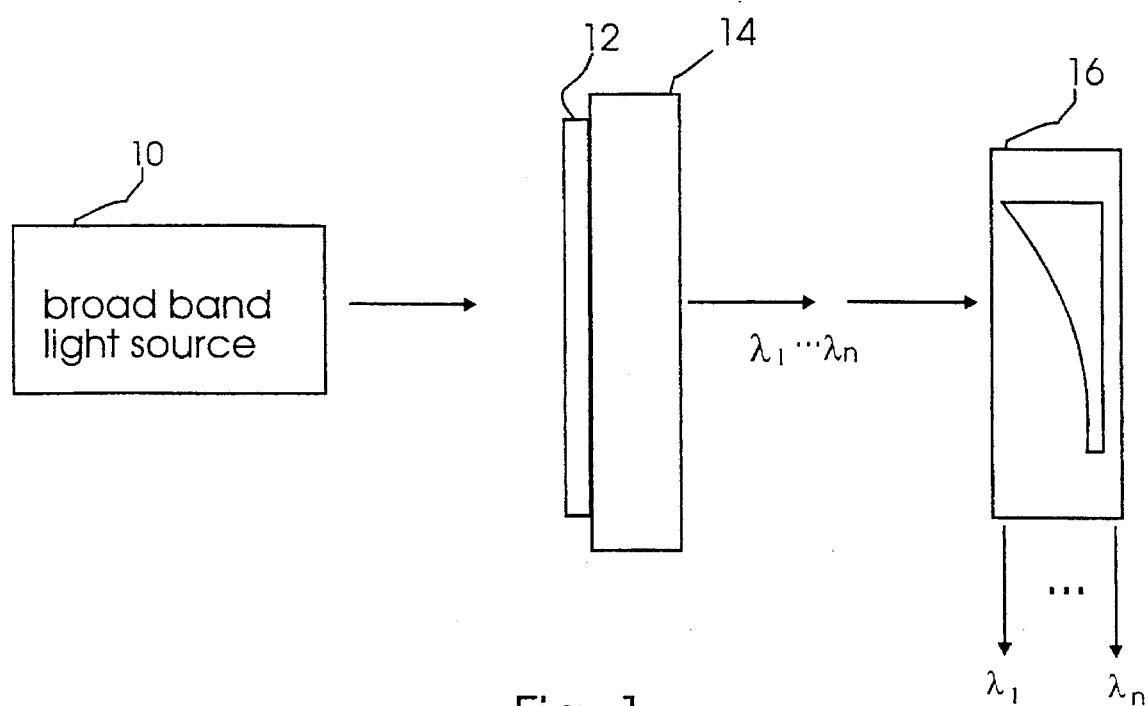
FIG. 1 is a schematic block diagram of a security system operable in a transmissive mode including a broadband light source, a thin film security device on the object to be protected, and a wavelength dispersive echelle grating detector.
Figure 1A:
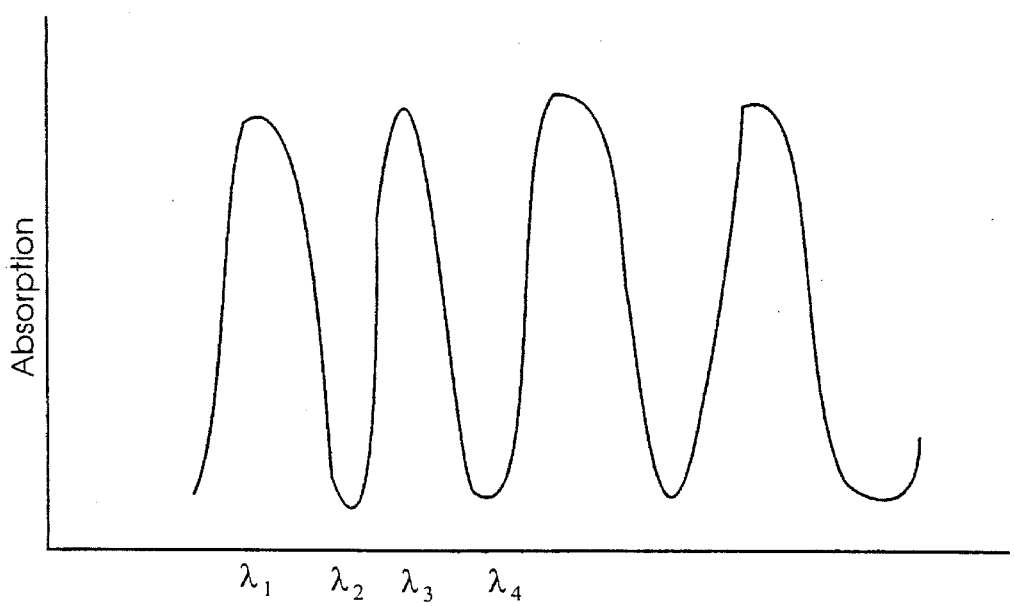

Referring now to FIG. 1, an embodiment of a system 5 is shown including a broadband light source 10 preferably in the form of a superluminescent diode (SLD) similar to the one described in III-Vs Review Vol. 6 No 5 pages 41–44; the light source 10 is positioned adjacent a side of a film 12 coated substrate 14 being at least partially transmissive to some wavelengths emitted by the light source 10. Adjacent to the other side of the substrate 14 is a wavelength dispersive detector 16 such as an échelle grating or spectrometer for detecting particular wavelengths of light that substantially propagate through the substrate 14.

An échelle grating-curved wavelength demultiplexer is described by M. Fallahi et at. in a paper entitled Demonstration of Demultiplexer in GaAs/AlGaAs Suitable for Integration, in Electronics Letters 19th Nov., 1992 Vol. 28 No 24 at page 2217. As well, J. B. D. Soole et at. in a paper entitled Monolithic InP/InGaAsP/InP grating spectrometer for the 1.48–1.56 mm wavelength range in Appl. Phys. Lett. Vol. 58, No. 18, published May 6, describe a method and device for separating specific incoming wavelengths of light. Since the thin film coating 12 can be designed to at least partially reflect, transmit or absorb light of predetermined wavelengths, it is possible to deposit the coating layers such that the film 12 provides a decodable security key in the form of a code with predetermined desired features in the transmission, absorption, or reflection spectrum at particular wavelengths. For example, if the broadband light source emitted wavelengths over the range $l_1$ to $l_4$, the film coating 12 could be designed such that the predetermined wavelengths $l_1$ and $l_3$ were transmitted by the film and substrate and propagated through to the detector and the predetermined wavelengths $l_2$ and $l_4$ were attenuated or reflected not propagating through the film. In order to achieve this, the film 12 would have to substantially reflect or absorb wavelengths $l_2$ and $l_4$ thereby not allowing them to pass to the detector, as well the film would have to substantially transmit wavelengths $l_1$ and $l_3$ thereby allow these wavelengths to propagate to the detector. In this example of wavelength division multiplexing (WDM), a binary code of 1010 is decoded. Of course in a binary scheme, the number of detectable wavelengths is a function of the number of individual channels the detector 16 is capable of receiving, an n-channel detector being capable of detecting $2^n$ binary codes. In a more complex arrangement that will be described hereafter, a similar system can be provided that determines the presence and absence of particular wavelengths of light in less discretized steps allowing many more "signatures" or codes to be detected than in the binary embodiment mentioned heretofore. For example, the presence or absence of particular wavelengths may be relativistically determined. Various schemes may be used in the determination of whether a particular wavelength is present or absent. A threshold value may be established, wherein values above the threshold value are considered to be present, and wherein values below or equal to the threshold value are considered to be absent. The threshold value may be dynamic in the sense of it being variable and dependent upon any of a plurality of parameters. For example, if the strength of a signal determined to be present is relatively weak, then threshold may be lowered to compensate for such changes within the system. If the thin fill is soiled, or crumpled, a normally strong signal at a particular wavelength may be detected as a relatively weak signal, therefore, using a dynamic threshold that takes into account the relative intensities, may be advantageous. Simple circuitry (not shown) comprising a mirror to determine a 100 percent reading and a black surface to determine a zero reading would provide for this type of dynamic scaling to be done. This calibration may be performed to compensate for any sensitivity change in the system as is required or at regular intervals. Many other schemes may be envisaged for determining the presence or absence of particular wavelengths; for example, one may want to detect if $l_1$ is of a larger magnitude than $l_2$ within some predetermined limits; one may want to determine if $l_1$ is above a threshold value and if $l_2$ is below that threshold value. It may be desirous to determine if $l_1$ is within a particular range and $l_2$ within another particular range. Or one may want to determine relativistic values for example $l_1/l_2$ or $l_2/l_3$.

In summary, the presence and absence of light at the predetermined wavelengths may be a relative value, an absolute value, or alternatively may be determined with regards to being above or below a predetermined threshold or a dynamic threshold, within predetermined limits.

In addition to authenticating documents, currency, and a variety of objects such as opaque and non-opaque plastics and glass to which a thin film can be applied, an arrangement of this type could be used as an encoded pass-key. In such an embodiment, a key comprising a thin film coded filter is read by a detector 16 as shown in FIG. 1 and decoded by a logic circuit designed to validate certain keys by use of a look-up table of valid codes.

Figure 2:
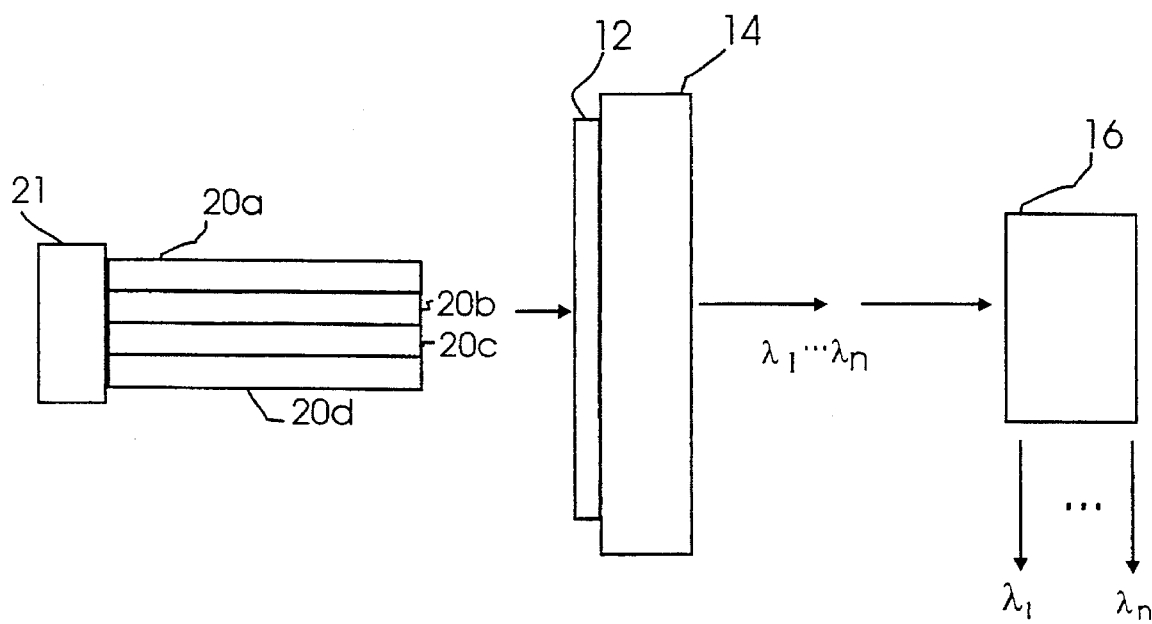
FIG. 2 is a schematic block diagram of a security system operable in a transmissive mode including four laser diodes, a thin film security device on the object to be protected, and a detector.
Figure 2A:
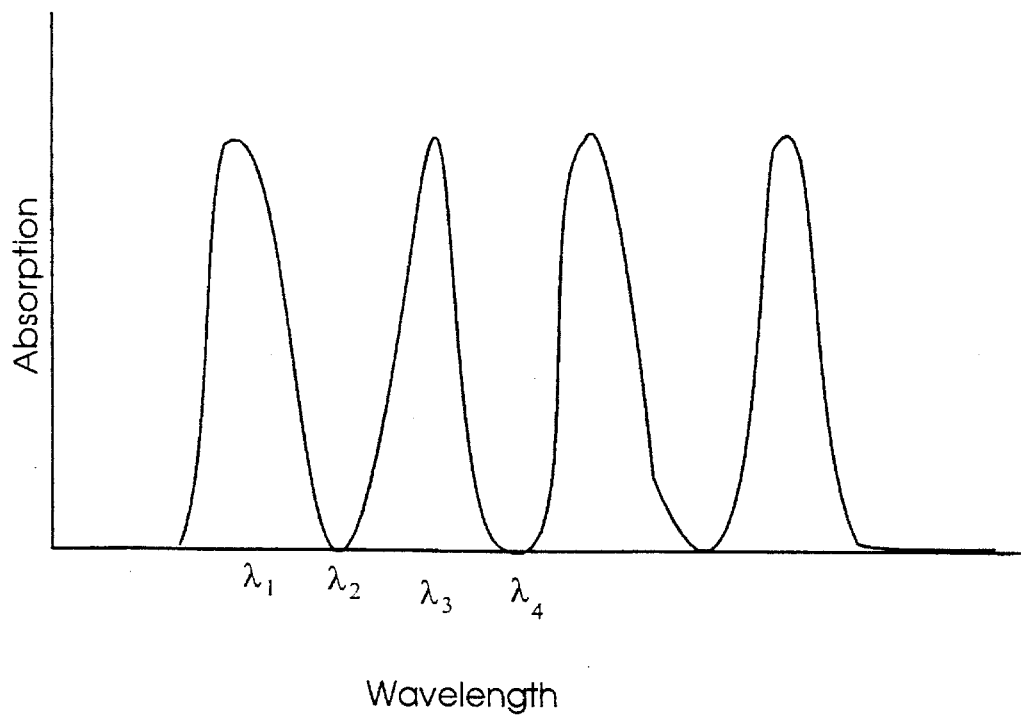

As an alternative to the systems described heretofore based on wavelength division multiplexing (WDM), FIG. 2 shows an arrangement using time division multiplexing (TDM). This is a matter of design choice and the decision to use TDM over WDM or vice versa may be based primarily on the cost and availability of components. An array of narrow band light sources 20a, 20b, 20c, and 20d designed to emit wavelengths $l_1$, $l_2$, $l_3$ and $l_4$ respectively is shown connected to a timing circuit 21. A means for producing a light source capable of emitting a plurality narrow band light wavelengths is described by G. Raybon et al. in a paper entitled 1.7 Gbit/S Transmission Over 217 Km Using A 16×1 Photonic Integrated Circuit Transmitter, published in Electronics Letters, Jul. 8, 1993, vol. 29 no. 14 at page 1295. G. Raybon et al. describe a device capable of transmitting a plurality of channels to obtain wavelengths over 1.545 and 1.555 mm and an average channel spacing of 6.7 Å. Another device having similar characteristics is described by J. B. D. Soole et al. in a paper entitled Wavelengths-Selectable Laser Emission From a Multistripe Array Grating Integrated Cavity Laser, published in Appl. Phys. Lett. 61 (23) 7 Dec. 1992 on page 2750. Soole's device is capable of transmitting 15 wavelengths, evenly spaced by 2 nm in the 1.5 mm band. The timing circuit 21 ensures that only one of the narrow band light sources is mined on at a time. A thin film 12 applied to a substrate 14 is positioned intermediate the light sources and a broad band detector 26. The film 12 is identical to the one used in the previous example although the layers could be varied and therefore encoded in a different manner to match the wavelength range of the light sources. After the timing circuit switches on light source 20a it sequentially switches on 20b, 20c, and 20d; the detector, capable of detecting light over the wavelength range of the light sources, is simultaneously switched on or can remain on. A simple logic circuit (not shown) is capable of capturing the state of the detector 26, thereby decoding the wavelength specific code within the thin film 12. A comparator circuit not shown can be provided to compare the decoded binary number with one or more valid binary codes.

Figure 3:
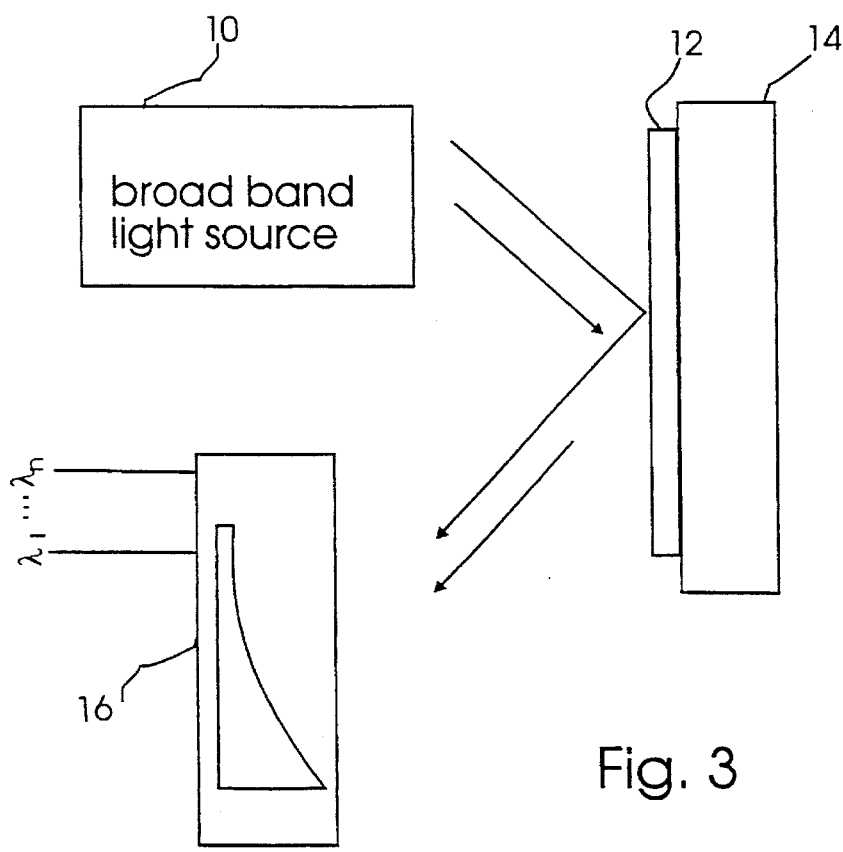
FIG. 3 is a schematic block diagram of a security system operable in a reflective mode including a broadband light source, a thin film security device on the object to be protected, and a wavelength dispersive echelle grating detector.
Figure 3A:
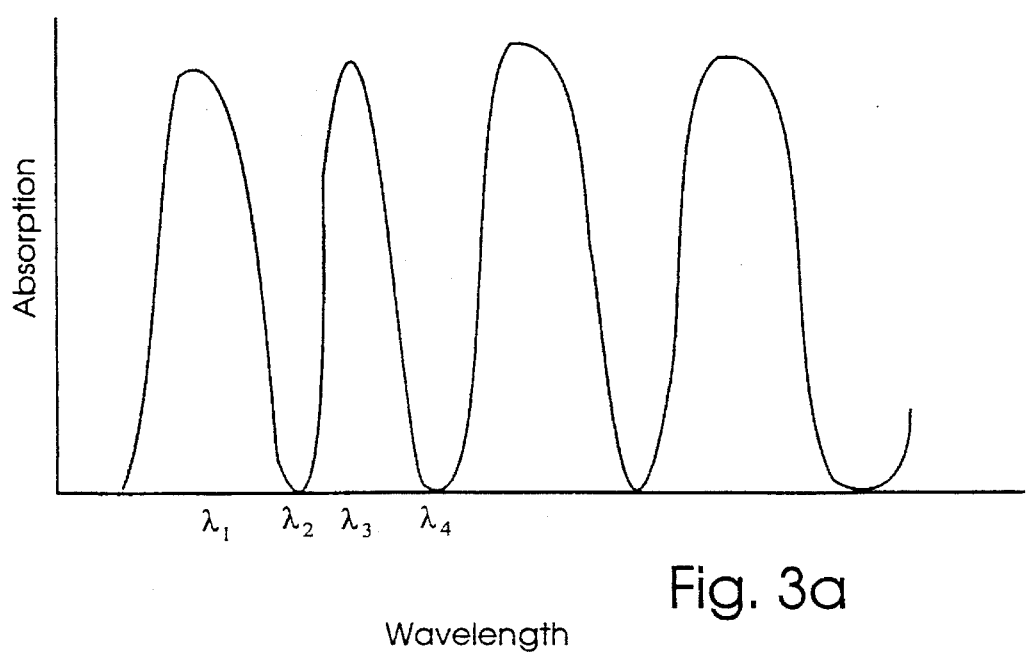

Both the WDM and the TDM circuits shown in FIGS. 1 and 2 respectively can be arranged in a different manner whereby the detector and light source are located on the same side as the film. This is illustrated by way of example in FIG. 3 for the WDM mode of operation. In this embodiment the film is designed to substantially reflect or transmit particular wavelengths of light and to substantially absorb other particular wavelengths. A reflected wavelength of light is detected by the detector and is decoded as a logic one; absorbed or transmitted wavelengths are not detected, their absence being decoded as a logic zero.

Figure 4:
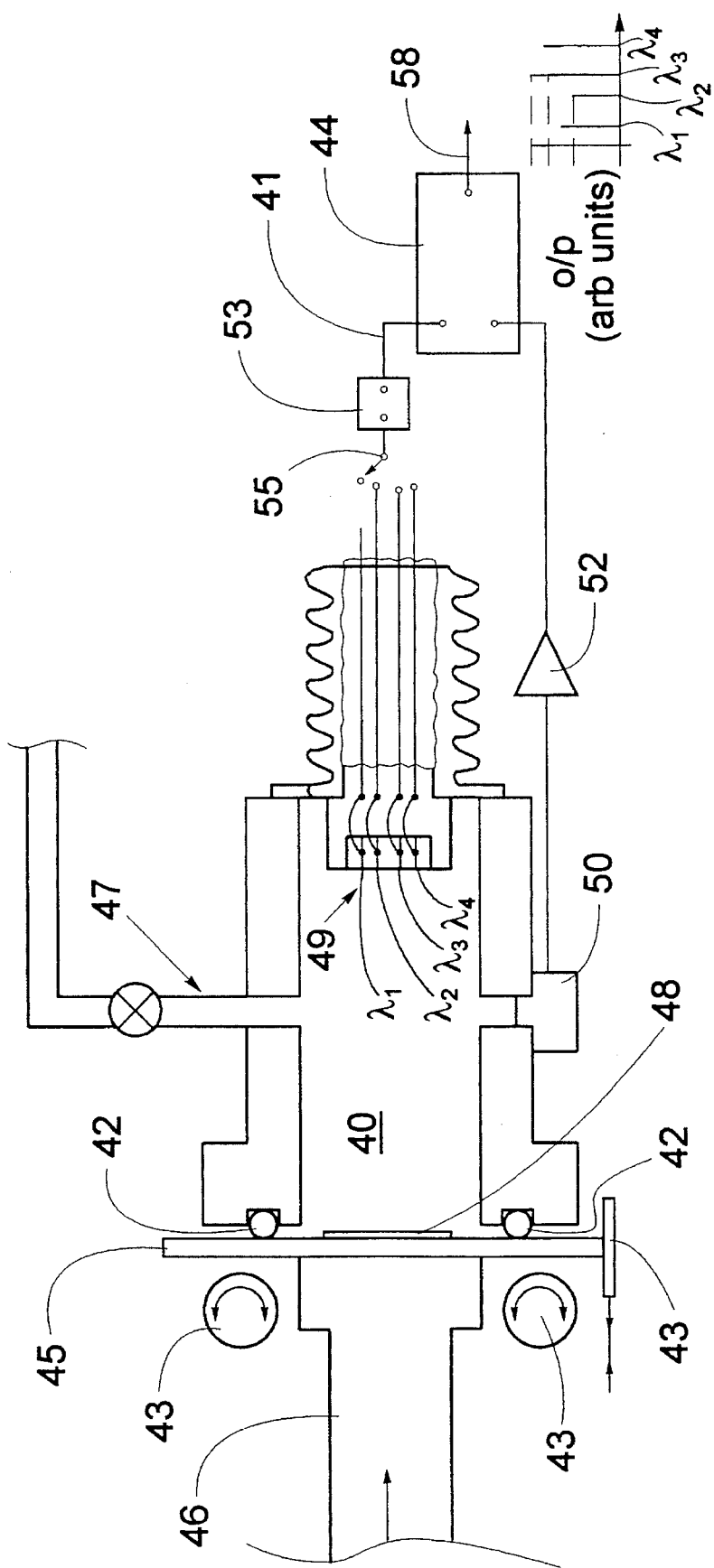
FIG. 4 is a schematic block diagram of an absorption detector for determining the authenticity of thin film coated card in accordance with the invention.

In an alternate embodiment of FIG. 4, an absorption detector is shown comprising an acoustic chamber 40 having an open end adjacent O-ring seals 42 for sealing with a credit card 45 face. The credit card is correctly positioned over the opening for detection by a mechanism 43 so that it completely covers the opening. A movable plunger 46 forces the credit card 45 in contact with the O-ring seals 42 forming the air tight acoustic chamber 40. The chamber 40 may be evacuated through a port 47, back-filled with a gas such as helium or nitrogen for improving the fixture position of the card 45 and for controlling the optical absorption properties in the acoustic chamber 40. The card 45 is coated with the thin film multilayer coating 48 having known absorption characteristics at predetermined wavelengths. Four laser diodes 49 each of a different wavelength are located at opposite the open end of the chamber and facing the thin film 48. The laser diodes are powered by a modulated power supply at a predetermined frequency and may be selectably switched on by a switch 55 to provide one of 4 modulated laser signals upon the film. A reference signal 41 is supplied to a phase sensitive detector 44.

In operation, when modulated light emitted from one of the selected lasers 49 impinges upon the thin film 48, it is absorbed. A photo-acoustic signal 58 is produced by the modulated laser signal and is detected by a microphone 50. The physical principles of the photo-acoustic effect are outlined by A Rosencweig and A Gersho in Vol. 47 page 64, Journal of Applied Physics 1976. The thermal and optical properties of the credit card 45 and film 48 are designed to provide a photo-acoustic signal. The signal 41 detected by the microphone 50 is amplified by an amplifier 52. The amplified signal is fed into a phase sensitive detector 44 and an output signal is produced, which is proportional to the absorption of the light by the film 48. By selecting different light source wavelengths it is possible to determine a signal proportional to the absorption of the film at a range of predetermined wavelengths.

Numerous other embodiments may be envisaged that do not depart from the spirit and scope of this invention.

What we claim is:

1. A system for authenticating a substrate, operable in one of a first mode, a second mode and a third mode of operation, the authenticating system in the first mode accepting a substrate coated with a thin film structure composed of layers having a combined thickness substantially within an order of of magnitude of the wavelength of light to be detected, said structure being capable of reflecting light of predetermined wavelengths and substantially absorbing or transmitting light of other predetermined wavelengths incident upon a same location on the surface of the substrate, in the second mode accepting a transmissive substrate coated with a thin film structure composed of layers having combined a thickness substantially within an order of of magnitude of the wavelength of light to be detected, said structure being capable of transmitting light of predetermined wavelengths and substantially absorbing or reflecting light of other predetermined wavelengths incident upon a same location on the surface of the substrate, and the system in the third mode accepting an absorbing substrate being coated with a coating capable of absorbing light of predetermined wavelengths and substantially reflecting or transmitting light of other predetermined wavelengths incident upon a same location on the surface of the substrate, the authenticating system comprising:

means for irradiating the substrate with predetermined wavelengths of coherent light; and, detecting means operable in a spectral range covering said predetermined wavelengths of coherent light to detect the presence or absence of said wavelengths of light when reflected, transmitted or absorbed, reflectively, from or by said thin film structure.

2. A method for authenticating one of (a) a reflective substrate coated with a thin film structure composed of layers having a combined thickness substantially within an order of magnitude of the wavelength of light to be detected, said structure being capable of reflecting light of predetermined wavelengths and substantially absorbing or transmitting light of other predetermined wavelengths incident upon a same location on the coating surface, (b) a transmissive substrate coated with a thin film structure composed of layers having a combined thickness substantially within in order of magnitude of the wavelength of light to be detected, said structure being capable of transmitting light of predetermined wavelengths and substantially absorbing or reflecting light of other predetermined wavelengths irradiating a same location on the coating surface, the method comprising the steps of:

irradiating the thin film structure with a single predetermined wavelength of substantially coherent light at a time; and, performing one of the following steps:

(i) in the case of the reflective coated substrate, detecting the presence or absence of said predetermined wavelength of light incident upon the location, within predetermined limits, that is substantially reflected by the coating;

(ii) in the case of the transmissive coated substrate, detecting the presence or absence of said predetermined wavelength of light incident upon the location, within predetermined limits, that is substantially transmitted by the coating; and, repeating the above step using a different wavelength of coherent light to obtain a sequence of respective presence or absence signals characteristic of said coating, wherein said thin film structure is designed to provide a distinctive spectral characteristics for said predetermined wavelengths in a non-visible part of the light spectrum.

3. A system for authenticating an article having thereon a coating composed of thin film layers having a combined thickness in the order magniude of the wavelength of light to be irradiated, said system comprising a source of a number of predetermined discrete wavelengths of coherent light in a non-visible range for irradiating said coating, and a detector for detecting the presence or absence of the predetermined wavelengths of light incident on said coating and either reflected therefrom or transmitted therethrough, wherein said coating has a distinctive spectral characteristics for said predetermined wavelengths.

4. The system according to claim 3 wherein said article and said coating are substantially transmissive at least at some of said predetermined wavelengths.

5. The system according to claim 3 wherein said coating is substantially reflective at least at some of said predetermined wavelengths.

6. The system according to claim 3 wherein said source is a number of single-wavelength sources of coherent light.

7. The system according to claim 3 wherein said source is a tunable source of light.

8. The device as defined in claim 3, wherein the detector is a single detector.

9. A method of authenticating an article having thereon a coating composed of thin film layers having a combined thickness in the order magnitude of the wavelength of light to be irradiated on said coating, said coating having a distinctive spectral characteristics at predetermined wavelengths of the light, said method comprising irradiating said coating with a discrete predetermined wavelength of coherent light at a time, detecting the presence or absence of the predetermined wavelength of said coherent light incident on said coating and either reflected therefrom or transmitted therethrough, and repeating said irradiating and detecting steps to obtain a sequence of presence and absence readings at the predetermined wavelengths of light, said sequence being indicative of the authenticity of said article.

10. The method of claim 9 wherein said coating and said article are substantially transmissive at least at some of the predetermined wavelengths.

11. The method of claim 9 wherein said coating is substantially reflective at least at some of the predetermined wavelengths.

* * * * *